(12) United States Patent
Matsumoto et al.

(10) Patent No.: US 7,678,185 B2
(45) Date of Patent: Mar. 16, 2010

(54) ANTHRAPYRIDONE COMPOUND OR SALT THEREOF, MAGENTA INK COMPOSITION CONTAINING THE SAME, AND COLORED PRODUCT

(75) Inventors: Hiroyuki Matsumoto, Kita-ku (JP); Noriko Kajiura, Kita-ku (JP); Yutaka Ishii, Kita-ku (JP); Yasuo Murakami, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/312,779

(22) PCT Filed: Nov. 28, 2007

(86) PCT No.: PCT/JP2007/072909

§ 371 (c)(1),
(2), (4) Date: May 26, 2009

(87) PCT Pub. No.: WO2008/066062

PCT Pub. Date: Jun. 5, 2008

(65) Prior Publication Data

US 2009/0286051 A1    Nov. 19, 2009

(30) Foreign Application Priority Data

Dec. 1, 2006  (JP) .............................. 2006-326196
Dec. 11, 2006  (JP) .............................. 2006-332828

(51) Int. Cl.
   *C09D 11/02*  (2006.01)
   *C09B 5/14*   (2006.01)
   *B32B 3/10*   (2006.01)
   *B41J 2/01*   (2006.01)

(52) U.S. Cl. ................... 106/31.47; 546/76; 428/195.1; 347/100

(58) Field of Classification Search .............. 106/31.47; 546/76; 428/195.1; 347/100
   See application file for complete search history.

(56) References Cited

U.S. PATENT DOCUMENTS 4,902,798 A    2/1990    Nakamatsu et al. ............ 546/76

(Continued)

FOREIGN PATENT DOCUMENTS

| JP | 63-139170 | 6/1988 |
| JP | 11-29714 | 2/1999 |
| JP | 2000-256587 | 9/2000 |

(Continued)

OTHER PUBLICATIONS

Machine translation of JP 2005/307068; Nov. 2005.*

International Search Report dated Jan. 8, 2008 (PCT/JP2007/072821 in co-pending U.S. Appl. No. 12/312,791).
The International Search Report dated Jan. 29, 2008 (PCT/JP2007/071631 in co-pending U.S. Appl. No. 12/312,274).

*Primary Examiner*—Helene Klemanski
(74) *Attorney, Agent, or Firm*—Nields, Lemack & Frame, LLC

(57) ABSTRACT

The present invention relates to an anthrapyridone compound represented by the following formula (1):

[Formula 1]

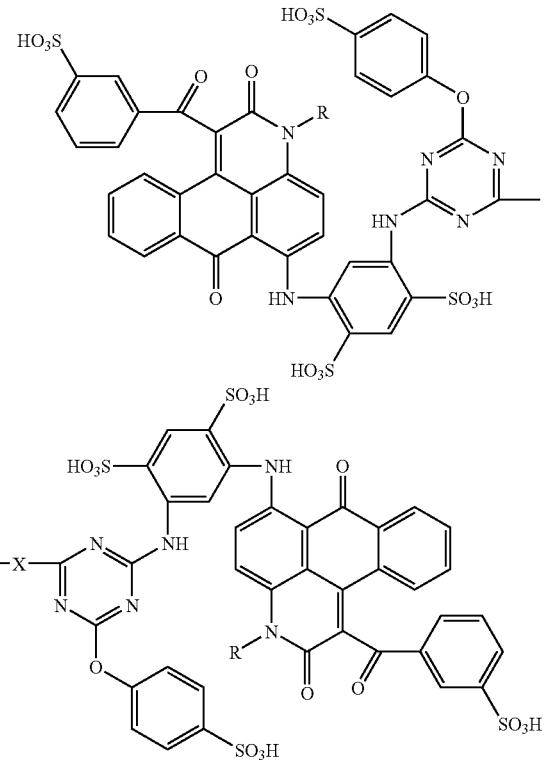

(1)

wherein, R represents a hydrogen atom, an alkyl group, a hydroxy lower alkyl group, a cyclohexyl group or a (mono- or di-alkylamino) alkyl group, X represents a cross-linking group represented by the formula:

$$-NH-(CH_2)n-NH- \quad (201)$$

wherein, n is 2 to 8
and another cross-linking group, respectively
or a salt thereof, a magenta ink composition containing the anthrapyridone compound, and a colored product therewith; said compound has a hue having a high vividness suitable for inkjet recording, a recorded matter therewith has strong fastnesses particularly such as light fastness and ozone fastness, and the ink composition has an excellent storage stability, whereby said compound is useful as a magenta coloring matter suitable for inkjet recording.

20 Claims, No Drawings

U.S. PATENT DOCUMENTS

| | | | |
|---|---|---|---|
| 5,367,075 A | 11/1994 | Nakamatsu et al. | 546/76 |
| 6,152,969 A | 11/2000 | Matsumoto et al. | 8/658 |
| 6,471,760 B1* | 10/2002 | Matsumoto et al. | 106/31.47 |
| 6,843,839 B2* | 1/2005 | Kanke et al. | 106/31.47 |
| 6,852,154 B2* | 2/2005 | Kitamura et al. | 106/31.47 |
| 6,929,361 B2* | 8/2005 | Matsumoto et al. | 106/31.47 |
| 6,984,032 B2* | 1/2006 | Kitamura et al. | 106/31.47 |
| 7,015,327 B2* | 3/2006 | Matsumoto et al. | 546/76 |
| 7,223,301 B2* | 5/2007 | Matsumoto et al. | 106/31.47 |
| 7,416,592 B2* | 8/2008 | Kitamura et al. | 106/31.47 |
| 7,618,484 B2* | 11/2009 | Fujimoto et al. | 106/31.47 |
| 2004/0239739 A1 | 12/2004 | Matsumoto et al. | 347/100 |
| 2005/0171351 A1 | 8/2005 | Matsumoto et al. | 546/76 |
| 2009/0047430 A1* | 2/2009 | Mori et al. | 347/100 |

FOREIGN PATENT DOCUMENTS

| | | |
|---|---|---|
| JP | 2001-354881 | 12/2001 |
| JP | 2003-335989 | 11/2003 |
| JP | 2005-307067 | 11/2005 |
| JP | 2005-307068 | 11/2005 |
| JP | 2006-083330 | 3/2006 |
| JP | 2007-77256 | 3/2007 |
| WO | 98/11167 | 3/1998 |
| WO | 03/027185 | 4/2003 |

* cited by examiner

ANTHRAPYRIDONE COMPOUND OR SALT THEREOF, MAGENTA INK COMPOSITION CONTAINING THE SAME, AND COLORED PRODUCT

TECHNICAL FIELD

The present invention relates to a novel anthrapyridone compound or a salt thereof, a magenta ink composition containing the anthrapyridone compound, and a colored product colored with this composition and the like.

BACKGROUND ART

In the recording method using an inkjet printer which is one of the typical methods among various color recording methods, various methods for discharging ink have been developed, and in any of them, ink droplets are generated and adhered onto various record-receiving materials (such as paper, film and cloth) to perform recording. This has been rapidly prevailing lately and is expected to continue growing remarkably in the future because of features such as quietness without noise generation due to no contact of a recording head with a record-receiving material and as easiness in downsizing, speeding up and colorizing.

Conventionally, as an ink for fountain pens, felt-tip pens or the like and as an ink for inkjet recording, water-based inks where a water-soluble dye is dissolved in an aqueous medium have been used. To these water-based inks, a water-soluble organic solvent is generally added in order to prevent ink from clogging at a pen tip or an inkjet nozzle. These conventional inks are required to provide recorded images with sufficient density, not to clog at a pen tip or a nozzle, to dry quickly on a record-receiving material, to bleed less, to have an excellent storage stability, and so on. In addition, formed images are required to have fastnesses such as water fastness, light fastness and moisture fastness.

Meanwhile, images or character information on color displays of computers are generally expressed by subtractive color mixing of 4 color inks of yellow (Y), magenta (M), cyan (C) and black (K), for color recording by an ink jet printer. In order that images expressed by additive color mixing of red (R), green (G) and blue (B) on CRT displays and the like is reproduced, as faithfully as possible, with images expressed by subtractive color mixing, it is desired that each of Y, M and C has a hue as close to each standard as possible and is also vivid. In addition, it is required that ink compositions are stable in storage for a long period of time, and that images printed therewith have a high concentration and also said images are excellent in fastnesses such as water fastness, light fastness, and gas fastness.

The application of inkjet printers has been widely spread in the fields ranging from small printers for office automation to large printers for industrial use, and therefore fastnesses such as water fastness, moisture fastness, light fastness and gas fastness have been required more than ever.

Water fastness has been largely improved by coating a paper surface with inorganic particles which can absorb the coloring matter in an ink, such as porous silica, cation polymer, aluminasol, special ceramic and the like, together with a PVA resin.

"Moisture fastness" means durability against a phenomenon that the dye in a record-receiving material bleeds during storage of the colored record-receiving material under an atmosphere of high humidity. Dye bleeding extremely deteriorates image quality of images particularly required to have a photo-like and high resolution image quality, and therefore it is important to reduce such bleeding as far as possible.

As for light fastness, any technique for large improvement thereof has not established yet. In particular, many of coloring matters for magenta among 4 primary colors of Y, M, C and K originally have low light fastness, and therefore improvement thereof is an important problem. In addition, with recent spread of digital cameras, there are more opportunities to print pictures at home, and image discoloration by oxidizing gas in the air where printed matters obtained are stored is acknowledged as a problem. The oxidizing gas reacts with dyes on or in a recorded paper, causing discoloration or fading of the printed image. Among oxidizing gasses, ozone gas is regarded as a causative agent accelerating color-fading phenomenon of inkjet-recorded images. This phenomenon of discoloration or fading is characteristic of inkjet images, and therefore improvement of ozone gas fastness is also an important problem.

As a magenta coloring matter used in water-based inks for inkjet recording, typical are xanthene-based coloring matters and azo based coloring matters using H acid. However, xanthene-based coloring matters are very excellent in hue and vividness but very inferior in light fastness. On the other hand, some of the azo-based coloring matters using H acid are good in terms of hue and water fastness, but many are inferior in light fastness, gas fastness and vividness. As for this type, a magenta dye excellent in vividness and light fastness has been developed but it still has a low level in light fastness compared with dyes having a different hue such as a cyan dye represented by a copper phthalocyanine-based coloring matter and a yellow dye.

Examples of the magenta coloring matter excellent in vividness and light fastness include an anthrapyridone-based coloring matter (see, for example, Patent Literatures 1 to 12), but a coloring matter for magenta satisfying all the requirements for hue, vividness, light fastness, water fastness, gas fastness and solution stability has yet to be obtained.

In particular, Patent Literatures 9 and 12 disclose a compound having a structure of cross-linking two molecules of anthrapyridone compounds with a cross-linking group, and an ink composition containing said compounds.

Patent Literature 1: JP H10-306221 A (pp. 1 to 3 and 7 to 18)
Patent Literature 2: JP 2000-109464 A (pp. 1 to 2 and 8 to 12)
Patent Literature 3: JP 2000-169776 A (pp. 1 to 2 and 6 to 9)
Patent Literature 4: JP 2000-191660 A (pp. 1 to 3 and 11 to 14)
Patent Literature 5: JP 2000-256587 A (pp. 1 to 3 and 7 to 18)
Patent Literature 6: JP 2001-72884 A (pp. 1 to 2 and 8 to 11)
Patent Literature 7: JP 2001-139836 A (pp. 1 to 2 and 7 to 12)
Patent Literature 8: WO 2004/104108 (pp. 20 to 36)
Patent Literature 9: JP 2003-192930 A (pp. 1 to 4 and 15 to 18)
Patent Literature 10: JP 2005-8868 A (pp. 1 to 3 and 15 to 22)
Patent Literature 11: JP 2005-314514 A (pp. 1 to 3 and 15 to 20)
Patent Literature 12: WO 2006/075706

DISCLOSURE OF THE INVENTION

Problems to Be Solved by the Invention

It is an object of the present invention to provide a magenta coloring matter (compound) which is high in solubility in water, has a hue and vividness suitable for inkjet recording and enables a recorded matter excellent in light fastness, moisture fastness and gas fastness, and an ink composition containing it.

Patent Literatures 9 and 12 disclose a magenta coloring matter considerably improved in light fastness, moisture fastness and gas fastness, however, light fastness and gas fastness are not still satisfied.

Means of Solving the Problems

The present inventors have intensively studied to solve the above problems and found that an anthrapyridone compound represented by a particular formula can solve the above problems, and have now completed the present invention.

That is, the present invention relates to:
(1) An anthrapyridone compound represented by the following formula (1) or a salt thereof,

[Formula 1]

(1)

[Chemical structure of anthrapyridone compound with sulfonic acid and triazine groups]

(Wherein, R represents a hydrogen atom, an alkyl group, a hydroxy lower alkyl group, a cyclohexyl group or a (mono- or di-alkylamino) alkyl group, and X represents a cross-linking group, respectively)

(2) The anthrapyridone compound or a salt thereof according to the above (1), wherein R is a hydrogen atom, a C1 to C4 alkyl group, a hydroxy C1 to C4 alkyl group, a cyclohexyl group or a (mono- or di- C1 to C4 alkylamino) C1 to C4 alkyl group, the cross-linking group X is N,N'-hydrazinediyl or a group selected from the group consisting of the following formulas (201) to (207), Formula (201)

(201)

$$*-\overset{H}{N}-(\overset{H_2}{C})_n-\overset{H}{N}-*$$

(Wherein, n is 2 to 8, and the symbol * represents a binding site to each of two different triazine rings)

Formula (202)

(202)

[Structure with two cyclohexyl rings and $R^2$ substituents]

(Wherein, $R^2$ represents a hydrogen atom or a methyl group, and the symbol * represents a binding site to each of two different triazine rings)

Formula (203)

(203)

[Structure with benzene ring and two CH₂ linkers to NH]

(Wherein, the symbol * represents a binding site to each of two different triazine rings)

Formula (204)

(204)

[Structure with cyclohexane ring and two CH₂ linkers to NH]

(Wherein, the symbol * represents a binding site to each of two different triazine rings)

Formula (205)

(205)

[Structure with bicyclic ring system and CH₂-NH linkers]

(Wherein, the symbol * represents a binding site to each of two different triazine rings)

Formula (206)

(206)

$$*-N\underset{\diagup}{\diagdown}-(\overset{H_2}{C})_m-N\underset{\diagup}{\diagdown}-*$$

(Wherein, m is 2 to 4, and the symbol * represents a binding site to each of two different triazine rings)

Formula (207)

(207)

[Piperazine ring structure]

(Wherein, the symbol * represents a binding site to each of two different triazine rings)

(3) The anthrapyridone compound or a salt thereof according to (1) or (2), wherein R is a hydrogen atom, a C1 to C4 alkyl group, a hydroxy C1 to C4 alkyl group, a cyclohexyl group or a (mono- or di- C1 to C4 alkylamino) C1 to C4 alkyl group, and X is a group selected from N,N'-hydrazinediyl, the formula (201) where n is 2 to 6, the formula (202), the formula (203), the formula (204), the formula (205), the formula (206) where m is 3, or the formula (207), (4) The anthrapyridone compound or a salt thereof according to any one of the above (1) to (3), wherein R is a hydrogen atom, a linear C1 to C4 alkyl group, a 2-hydroxyethyl group, a cyclohexyl group or a 3-diethylaminopropyl group, and X is a group selected from the group consisting of the formula (201) where n is 2 to 4, the formula (202), the formula (203) and the formula (204), (5) The anthrapyridone compound or a salt thereof according to any one of the above (1) to (4), wherein R is a hydrogen atom or a linear C1 to C4 alkyl group, and X is a group of the formula (201) where n is 2 to 4, (6) The anthrapyridone compound or a salt thereof according to any one of the above (1) to (5), which is represented by the following formula (2),

[Formula 2]

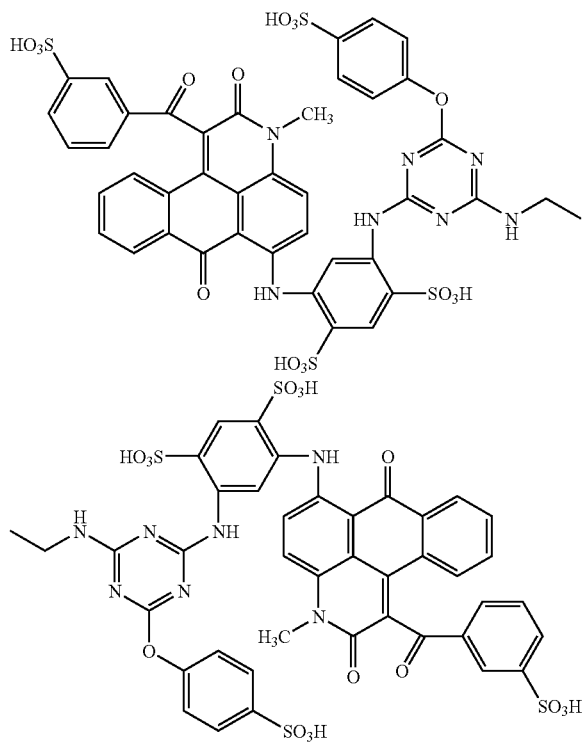

(2)

(7) An ink composition characterized by containing the anthrapyridone compound or a salt thereof according to any one of the above (1) to (6), (8) The ink composition according to the above (7), which contains water and a water-soluble organic solvent, (9) The ink composition according to the above (8), which is for inkjet recording,

(10) The ink composition according to any one of the above (7) to (9), wherein the content of an inorganic substance in the total amount of the anthrapyridone compound is 1% by weight or less,

(11) The ink composition according to any one of the above (7) to (10), wherein the content of the anthrapyridone compound is 0.1 to 20% by weight or less,

(12) An inkjet recording method characterized in that the ink composition according to any one of the above (7) to (11) is discharged responding to a recording signal to record on a record-receiving material,

(13) The inkjet recording method according to the above (12), wherein the record-receiving material is a communication sheet,

(14) The inkjet recording method according to the above (13), wherein the communication sheet has an ink receiving layer containing a porous white inorganic substance,

(15) A colored product colored with the ink composition according to any one of the above (7) to (11),

(16) The colored product according to the above (15), wherein coloring is carried out by an inkjet printer,

(17) An inkjet printer in which a container containing the ink composition according to any one of the above (7) to (11) is installed,

(18) The anthrapyridone compound or a salt thereof according to the above (1), wherein in the formula (1), R is a hydrogen atom or a C1 to C4 alkyl group and X is —NH(CH$_2$)$_{2-4}$NH—,

(19) An ink composition characterized by containing the anthrapyridone compound or a salt thereof according to the above (18),

(20) An ink composition characterized by containing the anthrapyridone compound or a salt thereof according to the above (6).

Effect of the Invention

The anthrapyridone compound of the above formula (1) of the present invention has the characteristics of exhibiting a hue having very high vivid and highly brightness on an inkjet recording paper, being excellent in water-solubility, and having a good filtration property to a membrane filter in the production process of ink compositions. In addition, the ink composition of the present invention using this compound is free from crystal precipitation and change in physical properties and color after storage for a long period of time, and thus has a good storage stability. And the anthrapyridone compound of the present invention provides an ideal magenta hue to a printed matter using it as a magenta ink for inkjet recording without selecting a record-receiving material (such as paper and film). Further, the magenta ink composition of the present invention makes it possible to faithfully reproduce hue of a photo-like color image on paper. Furthermore, even when recording is performed on a record-receiving material whose surface is coated with inorganic particles, such as inkjet special paper (film) for photo image quality, fastnesses such as light fastness, ozone fastness and moisture fastness are good, and a long-term storage stability of photo-like recorded image is excellent. Accordingly, the anthrapyridone compound represented by the above formula (1) is extremely useful as an ink coloring matter for inkjet recording.

BEST MODE FOR CARRYING OUT THE INVENTION

The present invention will be specifically explained.

The compound of the present invention or the anthrapyridone compound of the present invention is an anthrapyridone compound represented by the above formula (1) or a salt thereof.

In the present description, when the term "alkyl group" is described, said alkyl group include, for example, alkyl groups having 1 to 8 carbon atoms, such as methyl, ethyl, n-propyl, iso-propyl, n-butyl, sec-butyl, t-butyl, iso-butyl, n-pentyl, n-hexyl, n-heptyl or n-octyl. In addition, the term "alkyl" in explanation of the formulas (1) or (3) is used in the same meaning.

In addition, the term "lower alkyl group" is described herein, said lower alkyl group can include, among the above alkyl groups, alkyl groups typically having 1 to 6 carbon atoms, preferably alkyl groups having 1 to 4 carbon atoms and more preferably methyl, ethyl, n-propyl, iso-propyl, n-butyl, iso-butyl, sec-butyl and t-butyl.

In the present description, when the term "lower" is described for a group besides lower alkyl groups, for example lower alcohol and the like, it means that the alkyl moiety of said group has carbon atoms in the same range as the above unless otherwise specified.

Further, in the present description, superscript "RTM" stands for Registered Trademark.

In the above formula (1), R represents a hydrogen atom, an alkyl group, a hydroxy lower alkyl group, a cyclohexyl group or a (mono- or di-alkylamino) alkyl group.

Examples of the alkyl group for R can include the above groups, preferable are lower alkyl groups, and preferable lower alkyl groups and specific examples thereof are as described above. The alkyl group for R is more preferably a methyl group.

Preferable examples of the hydroxy lower alkyl group for R include a hydroxy C1 to C4 alkyl group. Specific examples thereof include, for example, hydroxymethyl, hydroxyethyl, hydroxypropyl or hydroxybutyl. The alkyl in the hydroxy lower alkyl group includes linear, branched and cyclic alkyl groups, and linear alkyl groups are preferred. In addition, the substitution position of the hydroxy in said alkyl may be any position, and, however, terminal substitution is preferable. Specific examples thereof are, for example, 2-hydroxyethyl, 3-hydroxypropyl and 4-hydroxybutyl.

Preferable examples of the mono alkylamino alkyl group for R include a mono C1 to C4 alkylamino C1 to C4 alkyl group. Specific examples thereof include, for example, mono methylaminopropyl, mono ethylaminopropyl and the like.

Preferable examples of the (dialkylamino) alkyl group for R include a (di- C1 to C4 alkylamino) C1 to C4 alkyl group. Specific examples thereof include, for example, (dimethylamino) propyl, (diethylamino) ethyl and the like.

Preferable examples of R described above are a hydrogen atom, a C1 to C4 alkyl group, a hydroxy C1 to C4 alkyl group, a cyclohexyl group or a (mono- or di- C1 to C4 alkylamino) C1 to C4 alkyl group, and more preferable examples thereof are a hydrogen atom, a linear C1 to C4 alkyl group, a 2-hydroxyethyl group, a cyclohexyl group or 3-diethylaminopropyl group. Further preferable examples of R are a hydrogen atom, a linear C1 to C4 alkyl group, a 2-hydroxyethyl group, a cyclohexyl group or a 3-diethylaminopropyl group.

R is preferably a hydrogen atom, an alkyl group (preferably a C1 to C4 alkyl group) or a cyclohexyl group and more preferably a hydrogen atom or an alkyl group (preferably a C1 to C4 alkyl group). R is most preferably a C1 to C4 alkyl group and particularly preferably a methyl group.

In the formula (1), X represents a cross-linking group.

Specific examples of X can include, for example, N,N'-hydrazinediyl or a group selected from groups represented by the above formulas (201) to (207). In this connection, in the present invention, N,N'-hydrazinediyl represents hydrazo shown by —NHNH—. Further, the symbol "*" shown in the formulas (201) to (207) represents a bonding position to each of two different triazine rings, and the bonding mode is a direct bond. In other words, a bond marked by the symbol "*" shown in each formula (201) to (207) represents a bond of each nitrogen atom, and each nitrogen atom is directly bonded to each of two different triazine.

In the formula (201), n typically represents an integer number of 2 to 8, preferably 2 to 6, further preferably 2 to 4 and particularly preferably 2.

In the formula (202), $R^2$ represents a hydrogen atom or methyl, the both of which are preferred. However, optionally, a hydrogen atom is more preferred.

In the formula (206), m represents an integer number of 2 to 4 and preferably 3.

X is preferably N,N'-hydrazinediyl, or a group represented by the formula (201) where n is 2 to 6, one of the formulas (202) to (205), or the formula (206) where m is 3 or the formula (207). In addition, X is also preferably a group represented by the formula (201), the formula (202), the formula (203) or the formula (204), and more preferably the formula (201) where n is 2 to 6 and more preferably 2 to 4. It is more preferred that X is a group represented by the formula (201) (preferably n is 2 to 6 and more preferably n is 2 to 4) or the formula (202). It is most preferred that X is a group represented by the formula (201). In this case, the group where n is 2 to 4 is preferred and —NHCH$_2$CH$_2$NH— where n is 2 is more preferred.

Preferable examples of the compound of the present invention can include a compound of the formula (1) where the cross-linking group X is a group selected from the group consisting of groups represented by the formulas (201) to (207). More preferable is a compound where the cross-linking group X is a preferable group, a more preferable group, a further preferable group or the like, which are described above. In this case, it is more preferred that R in the formula (1) is one of the preferable examples, the more preferable examples and the like which are described above.

The typical compounds among the above preferable examples of the compound of the present invention will be more specifically described below.

More specifically, preferable examples of the compound of the present invention can include a compound of the formula (1) wherein R is a hydrogen atom, a C1 to C4 alkyl group, a hydroxy C1 to C4 alkyl group, a cyclohexyl group or a (mono- or di- C1 to C4 alkylamino) C1 to C4 alkyl group, and X is N,N'-hydrazinediyl or a group selected from the group consisting of groups represented by the formula (201) where n is 2 to 6, the formulas (202) to (205), the formula (206) where m is 3, and the formula (207); more preferable examples thereof can include a compound of the formula (1) wherein R is a hydrogen atom, a linear C1 to C4 alkyl group, a 2-hydroxyethyl group, a cyclohexyl group or a 3-diethylaminopropyl group, and X is a group selected from the group consisting of the formula (201) where n is 2 to 4, the formula (202) (more preferably, where $R^2$ is a hydrogen atom), the formula (203) and the formula (204) (among them, more preferred is a compound wherein X is a group of the formula (201) where n is 2 to 4); and further preferable examples thereof can include a compound of the formula (1) wherein R is a hydrogen atom or a linear C1 to C4 alkyl group and X is a group of the formula (201) where n is 2 to 4.

In addition, the anthrapyridone compound of the formula (1) wherein the cross-linking group X is —NH(CH$_2$)$_{2-4}$NH—, or a salt thereof is one of the more preferable compounds. In this case, further preferred is a compound of the formula (1) wherein R is a hydrogen atom or C1 to C4 alkyl, and most preferred is a compound of the formula (1) wherein R is C1 to C4 alkyl.

The salt of the compound of the above formula (1) is a salt with an inorganic or organic cation. Said salt is preferably, for example, an alkali metal salt (for example, lithium salt, sodium salt or potassium salt) or a salt with an ammonium ion represented by the following formula (3) (ammonium salt or organic ammonium salt).

Formula (3)

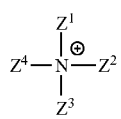
(3)

(Wherein, each of $Z^1$ to $Z^4$ independently represents a hydrogen atom, an alkyl group, a hydroxy alkyl group or a hydroxyalkoxyalkyl group.)

Examples of the alkyl group for $Z^1$ to $Z^4$ of the formula (3) include a methyl group, an ethyl group and the like, examples of the hydroxy alkyl group thereof include a hydroxymethyl group, a 2-hydroxyethyl group, a 3-hydroxypropyl group, a 2-hydroxypropyl group, a 4-hydroxybutyl group, a 3-hydroxybutyl group, a 2-hydroxybutyl group and the like, and examples of the hydroxyalkoxyalkyl group thereof include a hydroxyethoxymethyl group, a 2-hydroxyethoxyethyl group, a 3-hydroxyethoxypropyl group, a 3-hydroxyethoxybutyl group, a 2-hydroxyethoxybutyl group and the like.

Preferable examples among them include a sodium salt, a potassium salt, a lithium salt, a monoethanolamine salt, a diethanolamine salt, a triethanolamine salt, a monoisopropanolamine salt, a diisopropanolamine salt, a triisopropanolamine salt, an ammonium salt and the like. Particularly preferable among them are lithium, ammonium and sodium salts.

With regard to the production method of the above salt, for example, it is possible to obtain a sodium salt of the compound of the formula (1) as a wet cake by adding a sodium chloride to a reaction liquid containing the compound of the above formula (1) or to an aqueous solution dissolving a cake or dried form thereof in water, for salting out, and followed by filtration. In addition, it is possible to obtain a compound of the formula (1) in free acid form by dissolving the obtained wet cake again in water, then adding hydrochloric acid thereto for adjustment of the pH to 1 to 2, and separating obtained crystals by filtration. Further, it is also possible to obtain a mixture of the sodium salt and the free acid by appropriately adjusting to nearer neutral pH by controlling additional amount of hydrochloric acid, and separating obtained crystals by filtration. The mixture ratio of the both can be appropriately controlled by adjustment of the pH. Furthermore, while stirring a wet cake of the free acid together with water, for example, a potassium hydroxide, a lithium hydroxide, ammonia water, an organic base represented by the above formula (3), or the like is added to thereto in order to adjust the pH to alkali, so that each corresponding potassium salt, lithium salt, ammonium salt or organic salt can be obtained. In this connection, it is also possible to obtain a mixed salt of sodium and potassium or a mixture of sodium, potassium and the free acid by using a mixed wet cake of the free acid and the sodium salt and adding a potassium hydroxide thereto. Moreover, a mixture with another salt can be also obtained in the same manner. Preferable among these salts are lithium, ammonium and sodium salts as described above.

Preferable specific examples of the anthrapyridone compound represented by the formula (1) of the present invention are shown in the following Table 1.

TABLE 1

| Compound No. | R | X |
|---|---|---|
| 1 | Methyl | Formula (201); n = 2 |
| 2 | Methyl | Formula (202); R2 = hydrogen atom |
| 3 | Methyl | N,N'-Hydrazinediyl |
| 4 | Methyl | Formula (201); n = 4 |
| 5 | Methyl | Formula (201); n = 6 |
| 6 | Methyl | Formula (203) |
| 7 | Methyl | Formula (204) |
| 8 | Methyl | Formula (205) |
| 9 | Methyl | Formula (206); m = 3 |
| 10 | Methyl | Formula (207) |
| 11 | Hydrogen atom | Formula (201); n = 2 |
| 12 | Ethyl | Formula (201); n = 2 |
| 13 | 2-Hydroxyethyl | Formula (201); n = 2 |
| 14 | n-Butyl | Formula (201); n = 2 |
| 15 | Cyclohexyl | Formula (201); n = 2 |
| 16 | Diethylaminopropyl | Formula (201); n = 2 |
| 17 | Methyl | Formula (202); R2 = methyl |
| 18 | Hydrogen atom | Formula (201); n = 4 |
| 19 | Hydrogen atom | Formula (201); n = 6 |

The compound of the present invention can be obtained by, for example, the production method described below. In this connection, R and X shown in the following formulas (101) to (106), have the same meanings as in the above formula (1).

In a polar solvent such as xylene, 1 mol of an anthraquinone compound of the following formula (101) is reacted with 1.1 to 3 mol of ethyl benzoylacetate in the presence of a basic compound such as sodium carbonate at 130 to 180° C. for 5 to 15 hours to obtain a compound represented by the following formula (102).

Formula (101)

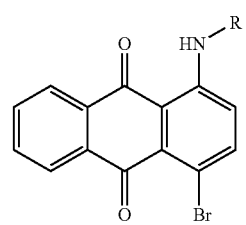
(101)

Formula (102)

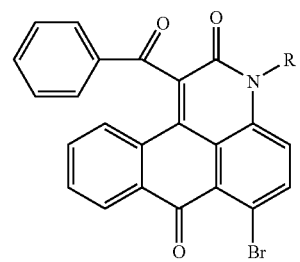
(102)

In an aprotic polar organic solvent such as N,N-dimethylformamide, 1 mol of the obtained compound of the above formula (102) is reacted with 1 to 5 mol of m-aminoacetoanilide is reacted (Ullmann reaction: condensation) in the presence of a base such as sodium carbonate and a copper catalyst such as copper acetate at 110 to 150° C. for 2 to 6 hours to obtain a compound of the following formula (103).

Formula (103)

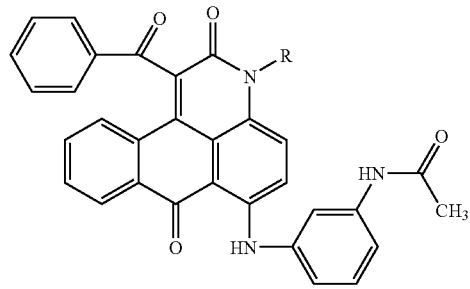

The obtained compound of the above formula (103) is sulfonated in 8 to 15% fuming sulfuric acid at 50 to 120° C. and simultaneously the acetylamino group is hydrolyzed, to obtain a compound represented by the following formula (104).

Formula (104)

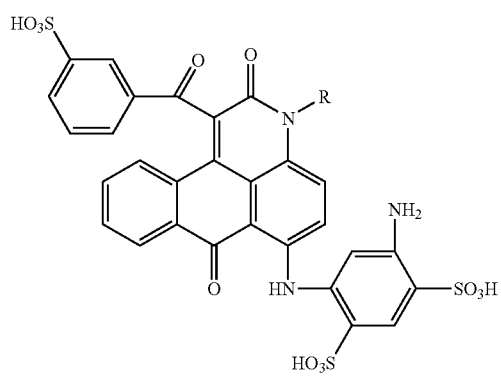

In water, 2 mol of the obtained compound of the above formula (104) is reacted with 2 to 2.4 mol of 2,4,6-trichloro-S-triazine (cyanuric chloride) at pH 2 to 7 and 0 to 35° C. for 2 to 8 hours to obtain a compound of the following formula (105). Said obtained compound is reacted with 2 mol of p-phenol sulfonic acid at pH 4 to 8 and 5 to 90° C. for 10 minutes to 5 hours to obtain a compound of the following formula (106).

Formula (105)

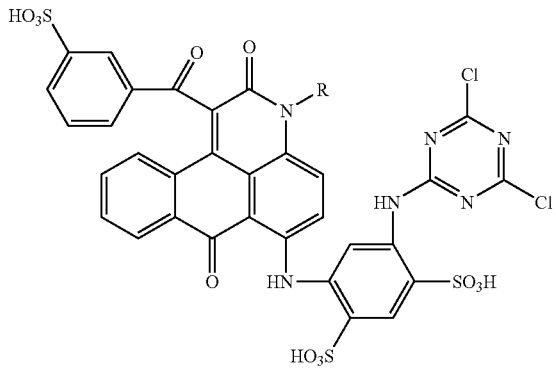

-continued

Formula (106)

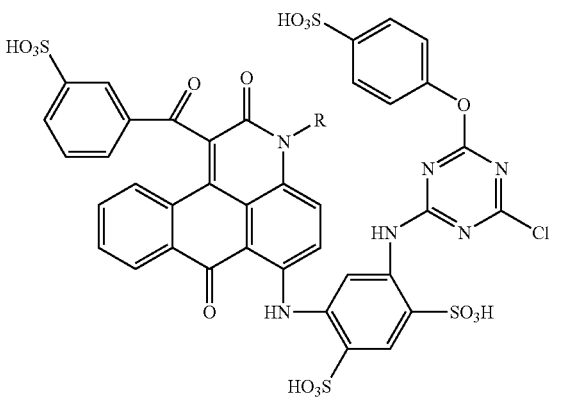

The obtained compound of the above formula (106) is reacted with 1 mol of a diamino compound corresponding to one of cross-linking groups represented by the above formulas (201) to (207) at pH 7 to 10 and 50 to 100° C. for 10 minutes to 8 hours. Thereby, a compound of the present invention represented by the above formula (1) can be obtained.

In this connection, the sequence order of the compounds to be condensed with 2,4,6-trichloro-s-triazine is appropriately determined according to the reactivity of each compound and therefore not limited to the above sequence order.

The compound represented by the above formula (1) can be obtained in free acid form or its salt form. These compounds of the present invention obtained as free acid or its salt according to necessity can be converted appropriately into an intended salt, for example, an alkali metal salt, an alkali earth metal salt, an alkyl amine salt, an alkanolamines salt, an ammonium salt or the like. The production methods where each salt is converted into free acid and where the free acid is converted into each salt, each mixed salt, or a mixture of the free acid and each salt are as described above.

When the compound of the present invention is used for production of ink compositions and the like, it is preferred to use the compound containing a smaller amount of inorganic impurities (inorganic substances) coexisting therein, such as metal cation chloride and sulfate salt. The content is, for example, about 1% by weight or less to the total amount of the compound of the present invention and the coexisting inorganic impurities, only as a guide. In order to produce a compound of the present invention containing a smaller amount of coexisting inorganic impurities, for example, the compound of the present invention obtained without desalting treatment by the above production method may be subjected to desalting treatment by a typically method with a reverse osmosis membrane.

The ink composition of the present invention can be obtained by dissolving the compound represented by the above formula (1) of the present invention or a salt thereof, together with ink preparation agents according to necessity, in water or an aqueous solvent (water containing a water-soluble organic solvent described later). In production of said ink composition, for example, a reaction liquid or the like containing the compound represented by the above formula (1) can be also directly used. In addition, it is possible that the intended product is isolated from the above reaction liquid, dried, for example spray-dried, and then used in production of the ink composition. The ink composition of the present invention contains typically 0.1 to 20% by weight, more preferably 1 to 15% by weight and further preferably 2 to 10% by weight of the compound of the present invention relative to the total amount of the ink composition. The ink composition of the present invention may contain 0 to 30% by weight and preferably 5 to 30% by weight of a water-soluble organic solvent and 0 to 10% by weight and preferably 0 to 5% by weight of ink preparation agents, respectively, and the rest is water.

Examples of the above water-soluble organic solvent include, for example, C1 to C4 alkanols such as methanol, ethanol, n-propanol, isopropanol, n-butanol, iso butanol, secondary butanol and tertiary butanol; carboxylic acid amides such as N,N-dimethylformamide and N,N-dimethylacetoamide; heterocyclic ureas such as 2-pyrrolidone, N-methyl-2-pyrrolidone, 1,3-dimethylimidazolidin-2-one and 1,3-dimethylhexahydropyrimid-2-one; ketones or keto alcohols such as acetone, methyl ethyl ketone and 2-methyl-2-hydroxypentan-4-one; cyclic ethers such as tetrahydrofuran and dioxane; mono-, oligo- or poly-alkylene glycols or thioglycols having a (C2 to C6) alkylene unit, such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, thiodiglycol, polyethylene glycol and polypropylene glycol; polyols (preferably triol) such as glycerine and hexane-1,2,6-triol; polyhydric alcohol (C1 to C4)alkyl ethers such as ethylene glycol monomethyl ether or ethylene glycol monoethyl ether, diethylene glycol mono methyl ether, diethylene glycol monoethyl ether or diethylene glycol mono butyl ether (butyl carbitol), and triethylene glycol monomethyl ether or triethylene glycol monoethyl ether; gamma-butyrolactone or dimethylsulfoxide; and the like.

Preferable among the above are isopropanol, glycerine, mono-, di- or tri-ethylene glycol, dipropylene glycol, 2-pyrrolidone, N-methyl-2-pyrrolidone and/or diethylene glycol mono butyl ether, and more preferable are isopropanol, glycerine, diethylene glycol mono butyl ether, 2-pyrrolidone and/or N-methyl-2-pyrrolidone. These water-soluble organic solvents are used alone or as a mixture thereof. Typically, 2 to 5 kinds, preferably 2 to 4 kinds, are preferably used in combination.

Hereinafter, ink preparation agents which can be used in preparation of the ink composition of the present invention will be explained. Specific examples of the ink preparation agents include, for example, an antiseptic and fungicide, a pH adjuster, a chelating agent, a rust preventive agent, a water-soluble UV absorbing agent, a water-soluble polymer compound, a dye dissolving agent, a surfactant and the like.

Examples of the antiseptic and fungicide include, for example, compounds such as organic sulfur-based, organic nitrogen sulfur-based, organic halogen-based, haloallylsulfone-based, iodopropargyl-based, N-haloalkylthio-based, nitrile-based, pyridine-based, 8-oxyquinoline-based, benzothiazole-based, isothiazoline-based, dithiol-based, pyridineoxide-based, nitropropane-based, organic tin-based, phenol-based, quaternary ammonium salt-based, triazine-based, thiadiazine-based, anilide-based, adamantane-based, dithiocarbamate-based, brominated indanone-based, benzyl bromoacetate-based, and inorganic salt-based compound.

Examples of the organic halogen-based compound include, for example, sodium pentachlorophenol.

Examples of the pyridineoxide-based compound include, for example, sodium 2-pyridinethiol-1-oxide.

Examples of the isothiazoline-based compound include, for example 1,2-benzoisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like.

Additional examples of the antiseptic and fungicides include sodium sorbate, sodium benzoate and the like (for example, trade name: Proxel® GXL(S), Proxel® XL-2(S) and the like; manufactured by Avecia Corp.) and in addition anhydrous sodium acetate and the like.

As the pH adjuster, any substance can be used as long as it can control the pH of the ink to be mixed in the range of 7.5 to 11.0 without any adverse effects on the ink. Examples thereof include, for example, alkanolamines such as diethanolamine and triethanolamine, alkali metal hydroxides such as lithium hydroxides, sodium hydroxides, potassium hydroxide and ammonium hydroxide, alkali metal carbonates such as lithium carbonate, sodium carbonate and potassium carbonate, and the like.

Examples of the chelating agent include, for example, sodium ethylenediamine tetraacetate, sodium nitrilotriacetate, sodium hydroxyethylethylenediamine triacetate, sodium diethylenetriamine pentaacetate, sodium uracil diacetate and the like.

Examples of the rust preventive agent include, for example, hydrogen sulfite salt, sodium thiosulfate, ammonium thioglycolate, diisopropylammonium nitrite, pentaerythritol tetranitrate, dicyclohexylammonium nitrite and the like.

Examples of the water-soluble UV absorbing agent include, for example, sulfonated benzophenon, sulfonated benzotriazole and the like Examples of the water-soluble polymer compound include, for example, polyvinyl alcohols, cellulose derivatives, polyamines, polyimines and the like.

Examples of the dye dissolving agent include, for example, urea, epsilon-caprolactam, ethylene carbonate and the like.

Examples of the surfactant include, for example, anionic surfactants, amphoteric surfactants, cationic surfactants, nonionic surfactants and the like.

Examples of the anionic surfactant include alkylsulfocarboxylate, alpha-olefin sulfonate, polyoxyethylene alkyl ether acetate, N-acyl amino acid and a salt thereof, N-acylmethyltaurine salt, alkylsulfate polyoxyalkyl ether sulfate, alkylsulfate polyoxyethylene alkyl ether phosphate, rosin acid soap, castor oil sulfate, lauryl alcohol sulfate, alkylphenol type phosphate ester, alkyl type phosphate ester, alkyl allylsulfonate, diethyl sulfosuccinate, diethylhexyl sulfosuccinate, dioctyl sulfosuccinate and the like.

Examples of the cationic surfactant include 2-vinylpyridine derivatives, poly(4-vinylpyridine) derivatives and the like.

Examples of the amphoteric surfactant include lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, and in addition, imidazoline derivatives and the like.

Examples of the nonionic surfactant include ethers such as polyoxyethylene nonylphenyl ether, polyoxyethylene octylphenyl ether, polyoxyethylene dodecylphenyl ether, polyoxyethylene octylphenyl ether, polyoxyethylene oleyl ether, polyoxyethylene lauryl ether and polyoxyethylene alkyl ether; esters such as polyoxyethylene oleic acid, polyoxyethylene oleate ester, polyoxyethylene distearate ester, sorbitan laurate, sorbitan monostearate, sorbitan monooleate, sorbitan sesquioleate, polyoxyethylene monooleate and polyoxyethylene stearate; acetylene alcohols such as 2,4,7,9-tetramethyl-5-decyne-4,7-diol, 3,6-dimethyl-4-octyne-3,6-diol and 3,5-dimethyl-1-hexyn-3-ol; and the like (for example, trade names: Surfynol® 104E, 104PG50, 82 and 465 and Olfine® STG which are manufactured by Nissin Chemical Industry Co., Ltd., and the like). These ink preparation agents are used alone or a mixture thereof.

The water-based ink composition of the present invention can produced by dissolving the compound of the present invention (hereinafter, also referred to as the present compound), together with the above ink preparation agents and the like according to necessity, in water or the above aqueous solvent (water containing a water-soluble organic solvent).

In the above production method, the sequence order of the components is not particularly limited. The present compound may be dissolved in water or the above water-soluble organic solvent in advance, and ink preparation agents may be added thereto; or the present compound may be dissolved in water and then a water-soluble organic solvent and/or ink preparation agents may be added thereto. In addition, the sequence order may be different from these, or a water-soluble organic solvent and ink preparation agents are added to a reaction liquid of the present compound or a coloring matter solution thereof after desalting treatment with a reverse osmosis membrane in order to produce the ink composition. In preparation of the ink composition, it is preferable that water to be used is water in which an amount of impurities is small such as ion-exchanged water or distilled water. Further, according to necessity, microfiltration may be carried out using a membrane filter or the like to remove foreign substances off, and furthermore, microfiltration is preferably carried out when the ink composition is used as an ink for inkjet printers. The pore size of a filter for microfiltration is typically 1 μm to 0.1 μm and preferably 0.8 μm to 0.2 μm.

The colored product of the present invention is a product colored with the above compound of the present invention. Materials to be colored are not particularly limited, and examples thereof include, for example, paper, fiber and cloth (cellulose, nylon, wool and the like), leather, substrates for color filters and the like, but are not limited thereto. Examples of coloration method include, for example, printing methods such as dip dyeing, textile printing and screen printing, and a method using an inkjet printer, and preferred is a method using an inkjet printer.

Examples of the record-receiving material (media) to which the inkjet recording method of the present invention can be applied include, for example, communication sheets such as paper and film, fiber, leather and the like. The communication sheets are preferably provided with surface treatment, specifically with an ink receiving layer on the substrate thereof. The ink receiving layer can be provided by, for example, impregnation or coating of a cation polymer on the above substrate, or by coating the above substrate surface with a porous white inorganic substance which can be absorb the coloring matter in the ink, such as porous silica, aluminasol and special ceramics, together with a hydrophilic polymer such as polyvinyl alcohol and polyvinyl pyrrolidone. The communication sheet provided with such an ink receiving layer is typically called inkjet special paper (film) and glossy paper (film), and examples thereof include, for example, Pictorico® (manufactured by Asahi Glass Co., Ltd.), Professional Photopaper, Super Photopaper and Matte Photopaper (which are all manufactured by Canon Inc.), CRISPIA®, Photo Paper (glossy), Photo Matte Paper and Super Fine Glossy Film (which are all manufactured by Seiko Epson Corporation), Advanced Photo Paper, Premium Plus Photo Paper, Premium Glossy Film and Photo Paper (which are all manufactured by Hewlett Packard Japan, Ltd.), PhotoLikeQP (manufactured by KONICA Corporation), and the like. In addition, plain paper can be naturally used.

Above all, it is known that the images recorded on the record-receiving materials whose surface coated with a porous white inorganic substance particularly have a more significant discoloration or fading by ozone gas. The water-based magenta ink composition of the present invention has an excellent fastness against gases including ozone gas and therefore it has an effect especially on images recorded on such a record-receiving material.

Examples of the porous white inorganic substance to be used for such an intended purpose include calcium carbonate, kaolin, talc, clay, diatom earth, synthesized amorphous silica, aluminum silicate, magnesium silicate, calcium silicate, aluminum hydroxide, alumina, lithopone, zeolite, barium sulfate, calcium sulfate, titanium dioxide, zinc sulfide, zinc carbonate and the like.

In order to record on a record-receiving material by the inkjet recording method of the present invention, for example, a container containing the ink composition of the present invention is placed in a predetermined position of an inkjet printer and recording may be carried out on a record-receiving material in a typical manner. In the inkjet recording method of the present invention, not only magenta of the present invention but also ink compositions of other colors such as yellow, cyan, green, orange and blue (or violet), and black according to necessity, can be used in combination. Each color ink composition is filled into each container, which is then placed (installed) in a predetermined position of an inkjet printer in the same manner for the container containing the water-based magenta ink composition for inkjet recording of the present invention, and used. Examples of the inkjet printer include, for example, a piezo type inkjet printer utilizing mechanical vibration, a bubble jet® type printer utilizing foam generated by heating, and the like.

The ink composition of the present invention exhibits a vivid magenta color, provides a highly vivid hue particularly to inkjet glossy paper, and enables recorded images excellent in fastnesses. In addition, it is highly safe to human beings.

The ink composition of the present invention is free from precipitation and separation during storage. In addition, when the ink composition of the present invention is used for inkjet recording, clogging does not occur at an injector (inkhead). The ink composition according to the present invention has no change in physical properties even in intermittent use of a continuous ink jet printer.

EXAMPLES

Hereinafter, the present invention will be more specifically explained with reference to Examples. In this connection, "part(s)" and "%" in Examples are based on weight unless otherwise specified.

Example 1

(1) To 360 parts of xylene, 94.8 parts of a compound of the following formula (4), 3.0 parts of sodium carbonate and 144.0 parts of ethyl benzoylacetate were added sequentially while stirring and the temperature was raised, and the reaction was carried out at 140 to 150° C. for 8 hours. Meanwhile, ethanol and water, which is produced during the reaction, were distilled out of the system as a xylene azeotrope to complete the reaction. Subsequently, the reaction liquid was cooled to 30° C., and 240 parts of methanol was added thereto and the mixture was stirred for 30 minutes to precipitate a solid, which was then separated by filtration. The resulting solid was washed with 360 parts of methanol and then dried to obtain 124.8 parts of a compound represented by the following formula (5) as pale yellow needle crystals.

Formula (4)

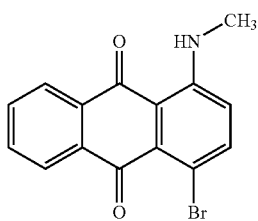

(4)

Formula (5)

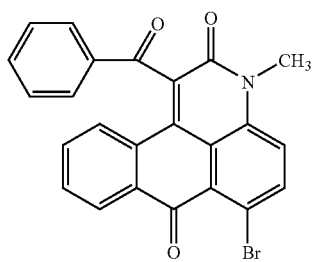

(5)

(2) Under stirring, 88.8 parts of the compound of the above formula (5), 75.0 parts of m-aminoacetoanilide, 24.0 parts of copper acetate monohydrate and 12.8 parts of sodium carbonate were sequentially added to 300.0 parts of N,N-dimethylformamide and the temperature was raised to 120 to 130° C., and the reaction was carried out for 3 hours. The reaction liquid was cooled to about 50° C., and 120 parts of methanol was added thereto and stirred for 30 minutes. The resulting precipitated solid was separated by filtration, washed with 500 parts of methanol followed by hot water at 80° C., and then dried to obtain 79.2 parts of a compound of the following formula (6) as bluish red crystals.

Formula (6)

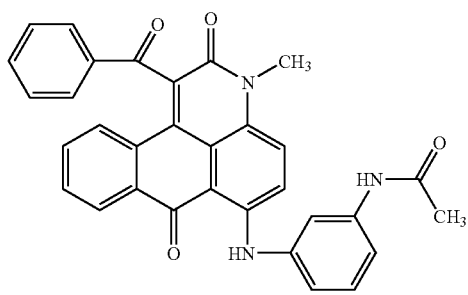

(6)

(3) Under stirring, 170 parts of 28% fuming sulfuric acid was added to 130 parts of 98% sulfuric acid while water-cooling to prepare 300 parts of 12% fuming sulfuric acid. Under water-cooling, 51.3 parts of the compound represented by the above formula (6) was added thereto at 50° C. or less, the liquid temperature was then raised to 85 to 90° C., and the reaction was carried out for 4 hours. The reaction liquid was added to 600 parts of ice water, and for the meantime, the liquid temperature raised by exothermic heat was maintained at 40° C. or less while adding ice. In addition, water was added to make the liquid volume 1000 parts and then filtered to remove off insoluble substances. Hot water was added to the resulting mother liquid to make the volume 1500 parts, and while maintaining the liquid temperature at 60 to 65° C., 300 parts of sodium chloride was added thereto and the mixture was stirred for 2 hours to precipitate crystals, which were then separated by filtration. The resulting crystals were washed with 300 parts of a 20% aqueous sodium chloride solution and water was well squeezed out to obtain 100.3 parts of a wet cake containing 59.2 parts of a compound of the following formula (7) as red crystals. In this connection, the purity of this compound was 45.9% by a diazo analysis method.

Formula (7)

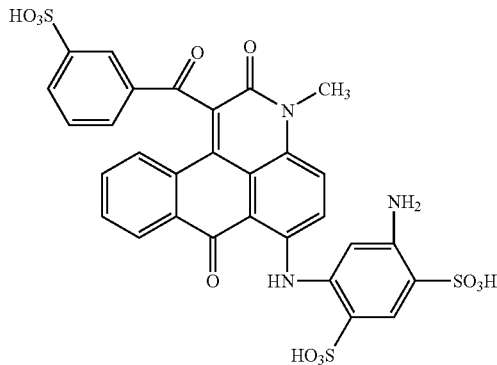

(7)

(4) To 60 parts of water, 67.7 parts of the wet cake of the above obtained compound represented by the formula (7) was added. Subsequently, 24 parts of a 25% aqueous sodium hydroxide solution was added thereto and the mixture was stirred, and in addition, the wet cake was dissolved while adjusting the pH to 3 to 4 by addition of a 25% aqueous sodium hydroxide solution.

Meanwhile, to 60 parts of ice water, 0.4 parts of LIPAL® OH (which is a trade name of an anionic surfactant, manufactured by Lion Corporation) was added, and 8.9 parts of cyanuric chloride was added thereto and the mixture was stirred for 30 minutes. The resulting suspension was then added to a solution containing the formula (7) described above, the pH was maintained to 2.7 to 3.0 with a 10% aqueous sodium hydroxide solution, and the reaction was carried out at 25 to 30° C. for 4 hours to obtain a reaction liquid containing a compound of the following formula (8).

Formula (8)

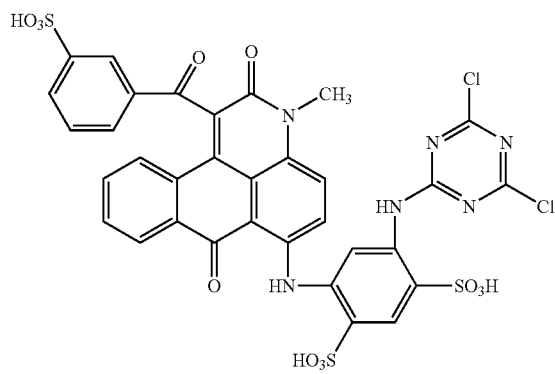

(8)

(5) To the above obtained reaction liquid containing the compound of the formula (8), 9.5 parts of sodium p-phenolsulfonate dihydrate was added, subsequently the liquid temperature was raised to 50 to 55° C. while maintaining the pH 6.5±0.3 by addition of a 25% aqueous sodium hydroxide solution, and the reaction was carried out at the temperature for 1 hour to obtain a reaction liquid containing a compound represented by the following formula (9).

Formula (9)

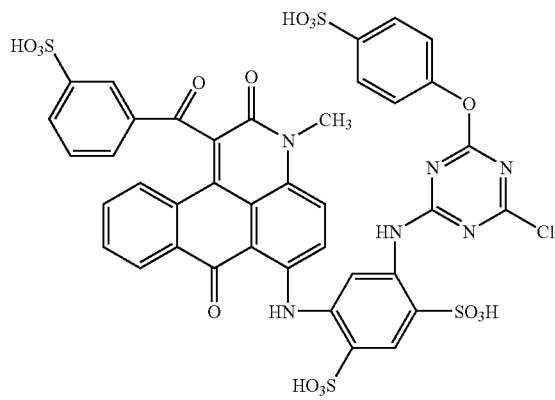

(9)

(6) To the above reaction liquid containing the compound of the formula (9) obtained in (5), 1.2 parts of ethylenediamine was added, the liquid temperature was raised to 78 to 82° C. while maintaining the pH to 7.8 to 8.2 by addition of a 25% aqueous sodium hydroxide solution, and the reaction was carried out at the temperature for 1 hour. After the reaction, water was added to adjust the liquid volume to about 350 parts, followed by filtration to remove off insoluble substances.

To the resulting mother liquid, water was added to make the liquid volume 400 parts, and then the pH was adjusted to 3 by addition of concentrated hydrochloric acid while maintaining the liquid temperature at 55±2° C. Subsequently, 40 parts of sodium chloride was added thereto over 15 minutes and the mixture was stirred for 30 minutes, and in addition, concentrated hydrochloric acid was added thereto to adjust the pH to 2. The resulting acidic aqueous solution was stirred for 1 hour to precipitate crystals, which were then separated by filtration. The obtained crystals were then washed with 100 parts of a 20% aqueous sodium chloride solution to obtain a compound represented by the above formula (2) of the present invention as a red a wet cake.

(7) The above wet cake obtained in (6) was added to 500 parts of methanol and heated to 60 to 65° C., followed by stirring for 1 hour. The resulting precipitated crystals were separated by filtration to obtain crystals, which were then washed with methanol, followed by drying to obtain 30.2 parts of a compound represented by the following formula (2) of the present invention (Compound No. 1 in Table 1) as red crystals. The λ max (maximum absorption wavelength) of the obtained compound in an aqueous solution was 509 nm.

In addition, the solubility of this compound in water (25° C.) was 200 g/L or more.

[Formula 2]

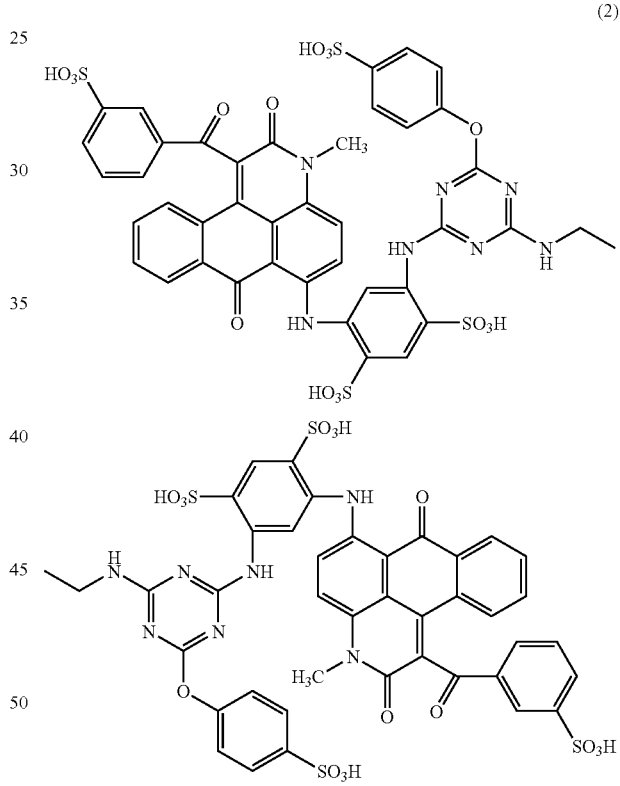

(2)

Example 2

(A) Preparation of Ink

Using the compound obtained in Example 1 described above (Compound No. 1), an ink composition having the composition ratio shown in Table 2 was prepared and filtered with a 0.45 μm membrane filter to obtain a water-based ink composition for inkjet recording. In addition, in the preparation of the above ink composition, ion-exchanged water was used as water, and water and a 25% aqueous NaOH (sodium hydroxide) solution was added so that finally, the pH of the ink composition was 8 to 10 and the total amount thereof was 100 parts. Further, in the test described later, using the above water-based ink composition for inkjet recording, inkjet recording was performed in the manner described later and evaluation of the recorded image was conducted in the manner described later.

TABLE 2

| Ink composition | |
|---|---|
| Compound of Example 1 (Compound Example No. 1) | 6.0 parts |
| Glycerine | 5.0 parts |
| Urea | 5.0 parts |
| N-methyl-2-pyrrolidone | 4.0 parts |
| Isopropylalcohol | 3.0 parts |
| Butyl carbitol | 2.0 parts |
| Surfynol 104PG50 (manufactured by Nissin Chemical Industry Co., Ltd.) | 0.1 part |
| Water + 25% NaOH | 74.9 parts |
| Total | 100.0 parts |

Comparative Example 1

For comparison, in the same manner as in Example 2 except that a compound of the following formula (10) disclosed in the example 3 of Patent Literature 9 (Compound No. 20) was used instead of the compound of Example 1 used in Example 2 described above, an ink composition having the same composition ratio as in Table 2 described above and a water-based ink composition for inkjet recording were prepared, inkjet recording was performed therewith, and evaluation of the recorded image was conducted in the same manner as in Example 2 described above.

[Formula 10]

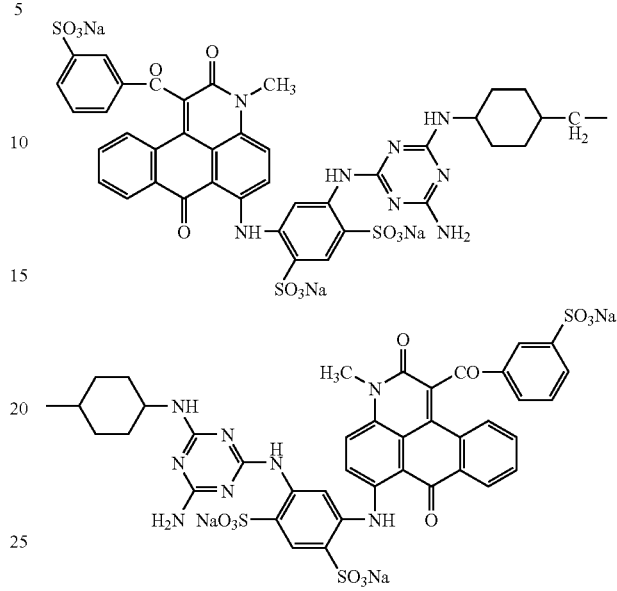

(10)

Comparative Example 2

For comparison, in the same manner as in Example 2 except that a compound of the following formula (11) disclosed in the example 1 of Patent Literature 12 (Compound No. 1 in the table 1 of Patent Literature 12) was used instead of the compound of Example 1 used in Example 2 described above, an ink composition having the same composition ratio as in Table 2 described above and a water-based ink composition for inkjet recording were prepared, inkjet recording was performed therewith, and evaluation of the recorded image was conducted in the same manner as in Example 2 described above.

Formula (11)

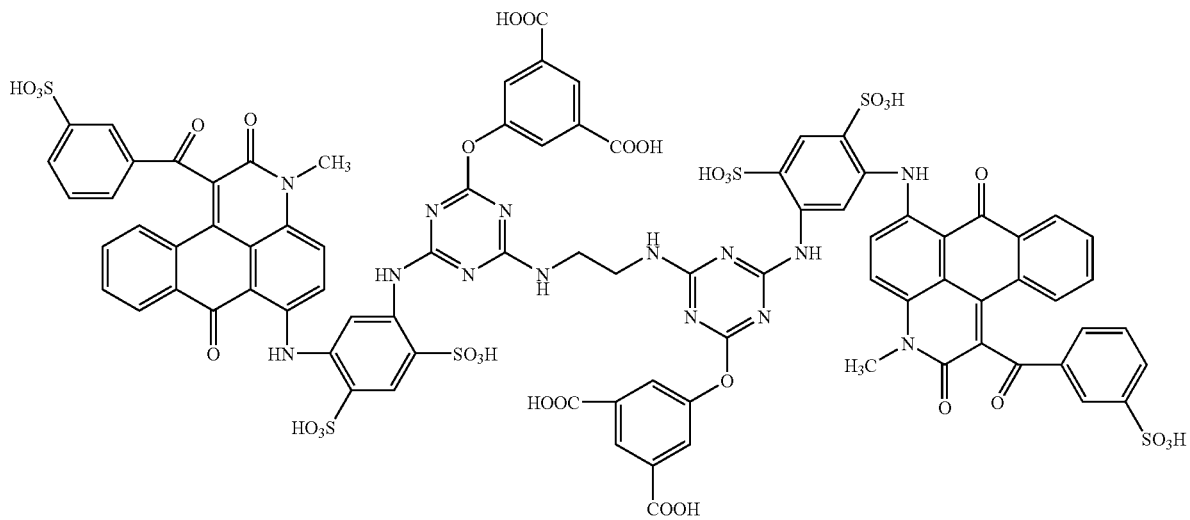

(11)

(B) Inkjet Printing

Using an inkjet printer (Pixus iP4100, manufactured by Canon Inc.), inkjet recording was performed on 2 types of glossy paper having an ink receiving layer containing a porous white inorganic substance. An image pattern was made so that several gradations of print density can be obtained in inkjet recording, and printed matters were prepared. In this connection, glossy papers used are as follows:

Glossy paper 1: Professional Photopaper PR-101 (which is a trade name, manufactured by Canon Inc.);

Glossy paper 2: CRISPIA® (which is a trade name, manufactured by Seiko Epson Corporation).

(C) Evaluation of Recorded Image

1. Hue Evaluation 1-1. Hue Evaluation of Glossy Paper

Hue and vividness of recorded image: Using a calorimetric system (GRETAG SPM50: manufactured by GRETAG-MACBETH AG), the recorded paper was measured in the part thereof where the print density (D value) was around 1.7, L*, a* and b* values were calculated, and $C^* = ((a^*)^2 + (b^*)^2)^{1/2}$ was calculated from the chromaticity (a*, b*) as for vividness. Hue evaluation was conducted by comparison with a sample of Standard Magenta of Japan Color of JNC (Japan Printing Machinery Manufacturers Association).

The results of the hue evaluation of Example 2 are shown in Table 3. In this connection, the paper used for Standard Magenta of Japan Color is Japan Color Standard Paper.

TABLE 3

|  | Brightness | Chromaticity | | Vividness |
|---|---|---|---|---|
|  | L* | a* | b* | C* |
| JNC Standard Magenta | 46.3 | 74.4 | −4.8 | 74.6 |
| Glossy paper 1 |  |  |  |  |
| Example 2 | 48.7 | 84.8 | −18.5 | 86.8 |
| Comparative Example 1 | 47.0 | 86.1 | −23.5 | 89.4 |
| Comparative Example 2 | 44.9 | 84.3 | −19.8 | 86.3 |
| Glossy paper 2 |  |  |  |  |
| Example 2 | 51.8 | 87.6 | −15.8 | 89.1 |
| Comparative Example 1 | 49.5 | 88.8 | −24.5 | 92.2 |
| Comparative Example 2 | 48.6 | 88.0 | −16.6 | 89.5 |

Judging from Table 3, it is found that with regard to any of the glossy papers, Example 2 and Comparative Example 2 have a hue approximate to that of JNC Standard Magenta, whereby the compounds used for these are suitable as a magenta coloring matter for inkjet. In addition, it is also found that C* values thereof are higher than that of JNC Standard Magenta, whereby they have a very vivid hue.

It is found that with regard to any of the glossy papers, b* value of Comparative Example 1 is lower than that of Example 1 or Comparative Example 2, whereby it has a bluish hue.

In addition, even when any of the glossy papers is used, L* value of Example 2 is higher than those of Comparative Examples 1 and 2, and judging from this, it is found that it has a very highly bright hue.

Judging from the above results, the recorded image with an ink composition using the coloring matter of the present invention has a hue close to JNC Standard Magenta and a higher brightness compared with JNC Standard Magenta and Comparative Examples 1 and 2. Therefore, it can be said that the anthrapyridone compound of the present invention has a hue and a brightness which are suitable for a magenta coloring matter for inkjet.

(D) Xenon Light Fastness Test of Recorded Image

Using a low temperature xenon weatherometer XL 75 (manufactured by Suga Test Instruments Co., Ltd.), test pieces prepared by printing on glossy papers 1 and 2 were put and irradiated at an illuminance of 100,000 Lux, a humidity of 60% RH and a temperature of 24° C. for 168 hours. The papers were measured for color difference (ΔE) before and after the test in the part thereof where D value was around 1.2, and evaluated.

The results are shown in Table 4.

(E) Ozone Gas Fastness Test of Recorded Image

Using an ozone weatherometer (manufactured by Suga Test Instruments Co., Ltd.), test pieces prepared by printing on glossy papers 1 and 2 were left for 8 hours under the circumstances of an ozone concentration of 10 ppm, a humidity of 60% RH and a temperature 24° C. The papers were measured for color difference (ΔE) before and after the test in the part thereof where D value was around 1.2, and evaluated.

The results are shown in Table 4.

TABLE 4

|  | Light fastness | Ozone gas fastness |
|---|---|---|
| Glossy paper 1 |  |  |
| Example 2 | 15.0 | 5.3 |
| Comparative Example 1 | 17.6 | 12.6 |
| Comparative Example 2 | 17.4 | 7.0 |
| Glossy paper 2 |  |  |
| Example 2 | 10.2 | 2.1 |
| Comparative Example 1 | 22.1 | 4.4 |
| Comparative Example 2 | 16.2 | 2.5 |

(F) Moisture Fastness Test of Recorded Image

Using a thermo-hygrostat (manufactured by Ohken Co., Ltd), test pieces prepared by printing on glossy paper 1 were left at 30° C. and 80% RH for 168 hours. The papers was judged for bleeding property by visual observation before and after the test in the part thereof where D value was around 1.7 and evaluated in the following 3 levels.

○: Bleeding is not observed
Δ: Bleeding is slightly observed
X: Bleeding is significantly observed As the results, bleeding was not observed in any of Example 2 and Comparative Examples 1 and 2, whereby ○ was marked in any of them as for evaluation.

Judging from Table 4, it is found that in the light fastness test using glossy paper 1, Example 2 has a color difference of 15 while Comparative Examples 1 and 2 have a larger value of color difference, respectively 17.6 and 17.4, whereby the degree of discoloration of Comparative Examples 1 and 2 is higher than that of Example 2

In addition, it is found that when glossy paper 2 is used, Example 2 has a color difference of 10.2 while Comparative Examples 1 and 2 have a much higher value, respectively 22.1 and 16.2, showing that a more significant difference is observed, whereby the degree of discoloration of Examples 1 and 2 using glossy paper 2 is much higher than using glossy paper 1. Judging from the above results, with regard to light fastness, Example 2 is more excellent than Comparative Example 1 and 2.

It is found that in the ozone gas fastness test using glossy paper 1, Example 2 has a color difference of 5.3 while Comparative Examples 1 and 2 have a larger value of color difference, respectively 12.6 and 7.0, whereby the degree of discoloration of Examples 1 and 2 is high.

Further, it is found that in the ozone gas fastness using glossy paper 2, Example 2 has a color difference of 2.1 while Comparative Examples 1 and 2 still have a larger value of color difference, respectively 4.4 and 2.5, whereby the degree of discoloration of Examples 1 and 2 is high.

Judging from the above results, it is found that with regard to ozone gas fastness, Example 2 is more excellent than Comparative Examples 1 and 2.

In the moisture fastness test, Example 1 and Comparative Examples 1 and 2 are equally good (○) because bleeding of any of them was not observed on any of the glossy papers.

Therefore, it is clear that the anthrapyridone compound of the present invention is a coloring matter which provides images also having fastnesses and in this regard, it can be said to be extremely excellent as a magenta coloring matter for inkjet.

[Formula 12]

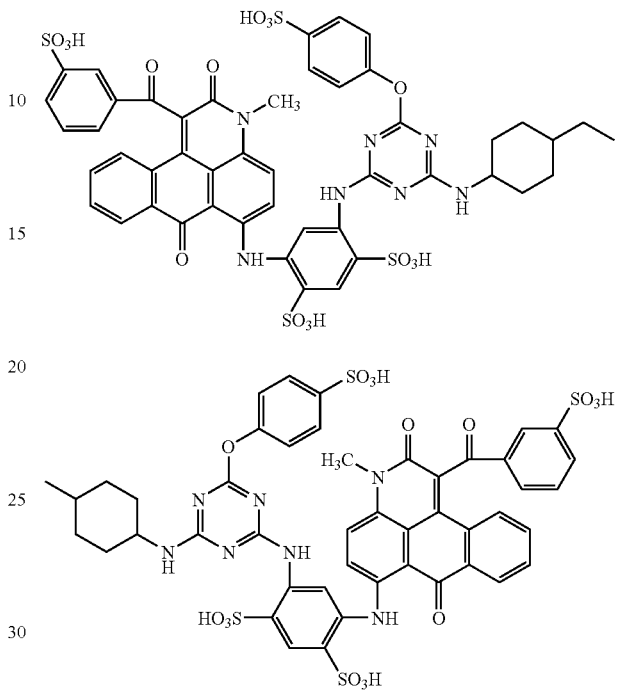

(12)

Example 3

(1) A reaction liquid containing a compound of the formula (9) obtained in the same manner as in (1) to (5) of Example 1 was raised in temperature to 90° C., 4.2 parts of 4,4'-diaminodicyclohexylmethane was added thereto, and then the reaction was carried out at 85 to 90° C. for 1 hour while maintaining the pH at 7.8 to 8.2 by addition of a 25% aqueous sodium hydroxide solution. After the reaction, water was added to adjust the liquid volume to about 350 parts, followed by filtration to remove off insoluble substances.

Water was added to the resulting mother liquid to adjust the liquid volume to about 400 parts, and then concentrated hydrochloric acid was added to adjust the pH to 2 while maintaining the liquid temperature at 55° C.±2° C. Subsequently, 40 parts of sodium chloride was added thereto over 15 minutes and further the mixture was stirred for 30 minutes. The resulting precipitated crystals were separated by filtration to obtain crystals, which were then washed with 100 parts of a 20% aqueous sodium chloride solution to obtain a compound represented by the following formula (12) as a red wet cake.

(2) The wet cake obtained in the above (1) was added to 500 parts of methanol, heated to 60 to 65° C., and stirred for 1 hour. The resulting precipitated crystals were separated by filtration to obtain crystals, which were then washed with methanol followed by drying to obtain 28.5 parts of a compound represented by the following formula (12) of the present invention (Compound No. 2 in Table 1) as red crystals. The λ max (maximum absorption wavelength) of the obtained compound in an aqueous solution was 517 nm.

Example 4

(1) To a reaction liquid containing a compound of the formula (9) obtained in the same manner as in (1) to (5) of Example 1, 2.7 parts of meta-xylylenediamine was added, the liquid temperature was raised to 78 to 82° C. while maintaining the pH at 7.8 to 8.2 by addition of a 25% aqueous sodium hydroxide solution, and the reaction was carried out at the temperature for 1 hour. After the reaction, water was added to adjust the liquid volume to about 350 parts, followed by filtration to remove off insoluble substances.

Water was added to the resulting mother liquid in order to adjust the liquid volume to about 400 parts and then concentrated hydrochloric acid was added to adjust the pH to 2 while maintaining the liquid temperature at 55° C.±2° C. Subsequently, 40 parts of sodium chloride was added thereto over 15 minutes and further stirred for 30 minutes. The resulting precipitated crystals were separated by filtration. The obtained crystals were then washed with 100 parts of a 20% aqueous sodium chloride solution to obtain a compound represented by the following formula (13) as a red wet cake.

(2) The wet cake obtained in the above (1) was added to 500 parts of methanol, heated at 60 to 65° C. and stirred for 1 hour. The resulting precipitated crystals were separated by filtration. The obtained crystals were then washed with methanol followed by drying to obtain 26.4 parts of a compound represented by the following formula (13) of the present invention (Compound No. 6 in Table 1) as red crystals. The λ max (maximum absorption wavelength) of the resulting compound in an aqueous solution was 518 nm.

Formula (13)

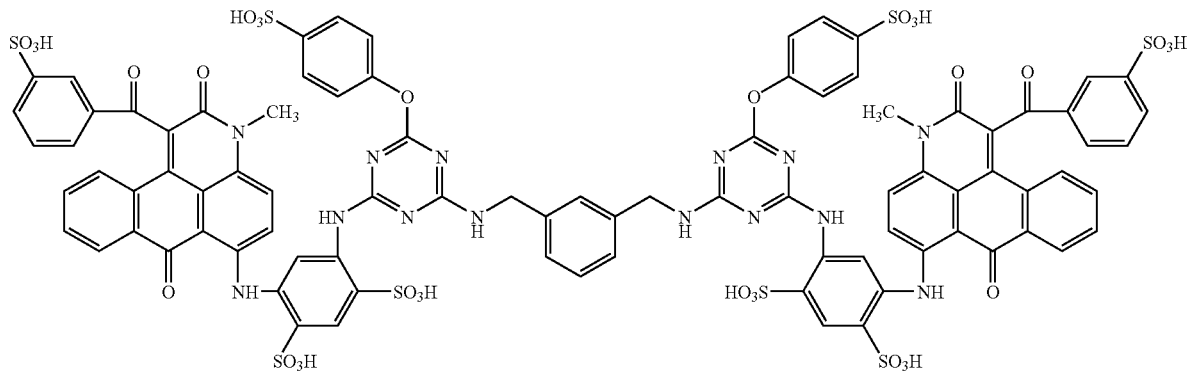

Example 5

(1) In a reaction liquid containing a compound of the formula (9) obtained in the same manner as in (1) to (5) of Example 1, 2.8 parts of 1,3-bis(aminomethyl)cyclohexane was added, the liquid temperature was raised in temperature to 78 to 82° C. while maintaining the pH at 7.8 to 8.2 by addition of a 25% aqueous sodium hydroxide solution, and the reaction was carried out at the temperature for 1 hour. After the reaction, water was added to adjust the liquid volume to about 350 parts followed by filtration to remove off insoluble substances.

Water was added to the resulting mother liquid to adjust the liquid volume to about 400 parts, and then concentrated hydrochloric acid was added to adjust the pH to 2 while maintaining the liquid temperature at 55° C.±2° C. Subsequently, 40 parts of sodium chloride was added thereto over 15 minutes and further stirred for 30 minutes. The resulting precipitated crystals were separated by filtration. The obtained crystals were then washed with 100 parts of a 20% aqueous sodium chloride solution to obtain a compound represented by the following formula (14) as a red wet cake.

(2) The wet cake obtained in the above (1) was added to 500 parts of methanol, heated at 60 to 65° C. and stirred for 1 hour. The resulting precipitated crystals were separated by filtration to obtain crystals, which were then washed with methanol followed by drying to obtain 31.2 parts of a compound represented by the following formula (14) of the present invention (Compound No. 7 in Table 1) as red crystals. The λ max (maximum absorption wavelength) of the obtained compound in an aqueous solution was 516 nm.

[Formula 14]

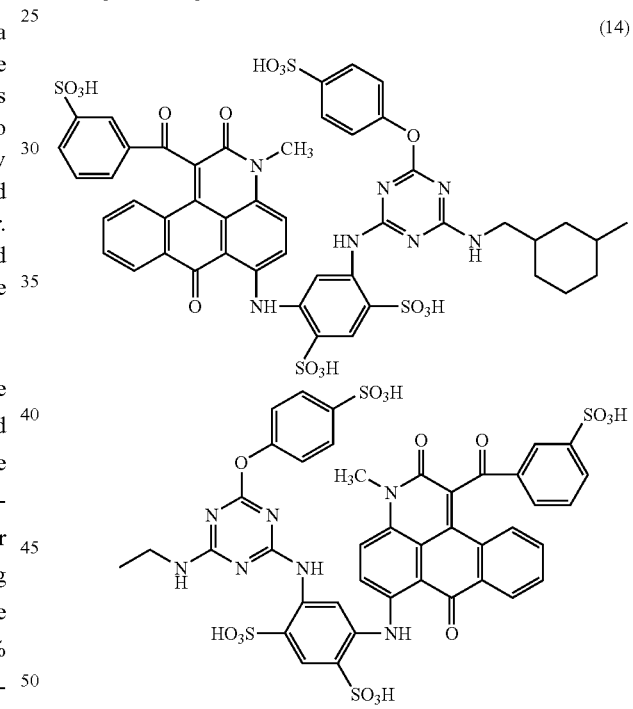

Comparative Example 3

For comparison, using a compound No. 29 (the following formula (A)) in the table 1 of Patent Literature 9, an ink composition was prepared in the same manner as in Example 2 (having the same composition ratio as in Table 2 except that the compound of the following formula (A) was used instead of the compound of Example 1 in Table 2), inkjet recording was performed therewith, and evaluation of the recorded images was conducted.

In this connection, the compound of the following formula (A) was synthesized as follows, according to Example 1 (5) described above.

To a reaction liquid containing a compound of the above formula (8) obtained in the same manner as in (1) to (4) of Example 1, 7.3 parts of sulfanilic acid was added. Subsequently, while maintaining pH 6.0±0.3 by addition of a 25% aqueous sodium hydroxide solution thereto, the liquid temperature was raised to 60° C. and the reaction was carried out at the temperature for 2 hours to obtain a reaction liquid containing a compound represented by the following formula (B). After that, 6.9 parts of a compound represented by the following formula (A) was obtained as red crystals according to the same operations as in (6) and (7) of Example 1 described above. The λ max (maximum absorption wavelength) of the obtained compound in an aqueous solution was 534 nm.

[Formula A]

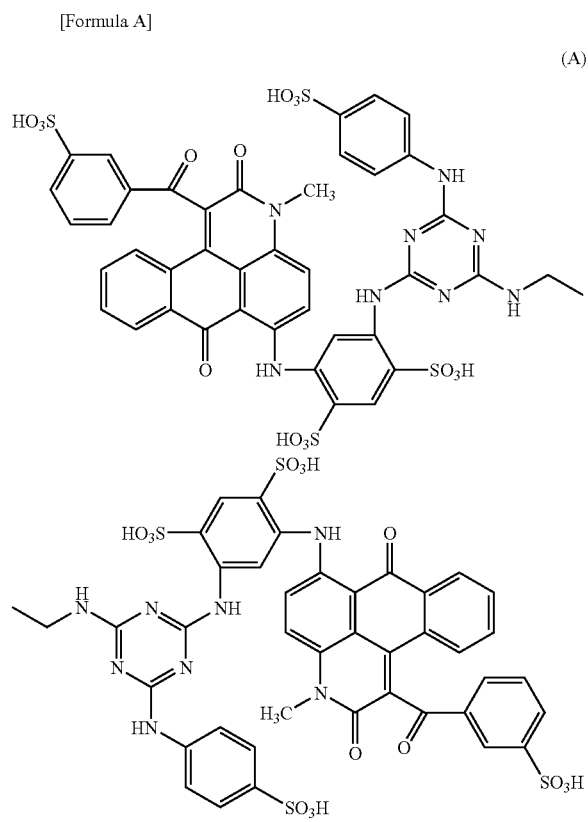

(A)

[Formula B]

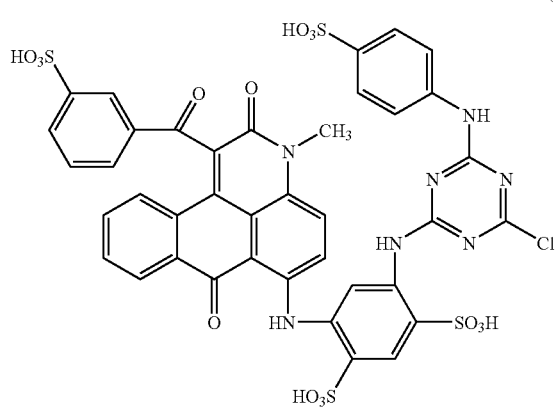

(B)

Comparative Example 4

Using an compound represented by the following formula (C) in the example 5 of Patent Literature 12 (Compound No. 4 in the table 1 of said Literature), an ink composition (having the same composition ratio as in Table 2 except that the compound of the following formula (C) was used instead of the compound of Example 1 in Table 2) was prepared in the same manner as in Example 2 described above, inkjet recording was performed therewith, and evaluation of the recorded image was conducted.

[Formula C]

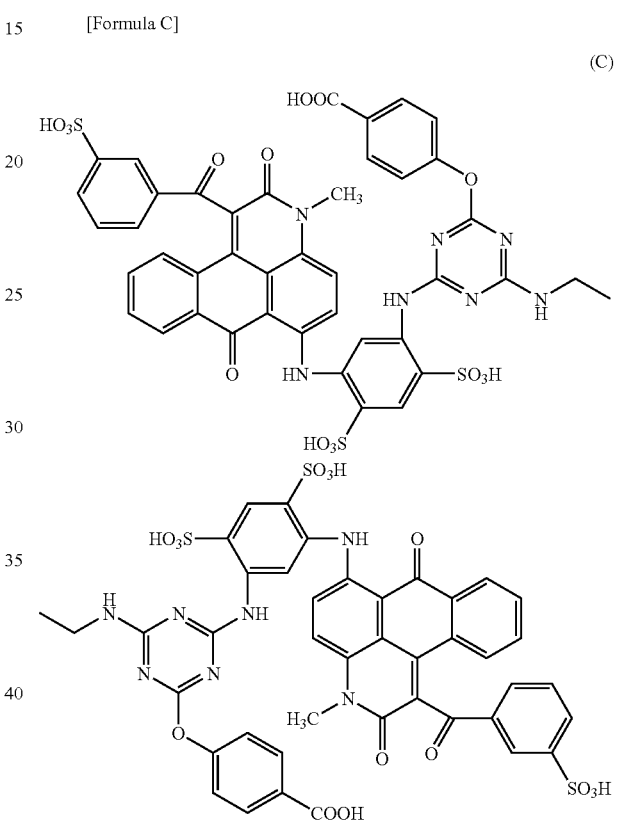

(C)

Inkjet Recording and Evaluation Result

With regard to inkjet recording for xenon light fastness test, ozone gas fastness test and moisture fastness test of recorded images, an image pattern was made in the same manner as in the section of (B) inkjet printing described above so that several gradations of print density can be obtained in inkjet recording and printed matters were prepared. In addition, for evaluation of print density, hue and vividness, in the same manner as in the section of (B) inkjet printing described above except that the ink compositions prepared in Example 2 and Comparative Examples 1 to 4 were used as they were to make printed matters without preparing the gradations of print density, printing was performed on the same 2 types of glossy paper as described above.

Glossy paper 1: Professional Photopaper PR101, which is a trade name, manufactured by Canon Inc.

Glossy paper 2: CRISPIA, which is a trade name, manufactured by Seiko Epson Corporation.

(C-1) Evaluation of Recorded Image:

Evaluation was conducted by the same method as that described in "(C) evaluation of recorded image" except that the above obtained recorded papers were used for color measurement. The results are shown in the following Table 5.

TABLE 5

|  | Brightness | Chromaticity | | Vividness |
|---|---|---|---|---|
|  | L* | a* | b* | C* |
| JNC Standard Magenta | 46.3 | 74.4 | −4.8 | 74.6 |

|  | Print density | Brightness | Chromaticity | | Vividness |
|---|---|---|---|---|---|
|  | D value | L* | a* | b* | C* |
| Glossy paper 1 | | | | | |
| Example 2 | 1.8 | 45.4 | 83.1 | −22.0 | 85.9 |
| Comparative Example 1 | 1.8 | 41.6 | 80.6 | −29.8 | 86.0 |
| Comparative Example 2 | 1.7 | 41.9 | 80.6 | −26.2 | 84.8 |
| Comparative Example 3 | 1.7 | 41.8 | 80.1 | −26.8 | 84.4 |
| Comparative Example 4 | 1.2 | 54.1 | 68.1 | −16.8 | 70.1 |
| Glossy paper 2 | | | | | |
| Example 2 | 1.9 | 44.8 | 82.6 | −21.8 | 85.4 |
| Comparative Example 1 | 1.8 | 44.5 | 83.2 | −29.7 | 88.4 |
| Comparative Example 2 | 1.8 | 42.9 | 82.1 | −22.1 | 85.0 |
| Comparative Example 3 | 1.8 | 43.9 | 82.5 | −25.4 | 86.3 |
| Comparative Example 4 | 1.2 | 54.2 | 67.3 | −17.3 | 69.5 |

As is clear from Table 5, the values of print density D of Example 2 and Comparative Examples 1 to 3 are in the range of about 1.7 to 1.9 in any of the glossy papers, showing that there is not a large difference between them while Example 2 has a better value of brightness (L*) in glossy paper 1 than Comparative Examples 1 to 3; and as for chromaticity (a*, b*), Comparative Examples 1 to 3 have a* values in glossy paper 1 which are lower and a little better than that of Example 2 while they have b* values which are further lower and worse than that of Example 2, showing that there is a large difference in b* value (in particular for Comparative Example 1), whereby Comparative Examples 1 to 3 have a bluish hue compared with Example 2. In addition, Comparative Example 4 has a high value of brightness (L*) compared with Example 2 and better values of chromaticity, a* value and b* value which are dose to those of JNC, but the print density, D value, thereof is 1.2, which is extremely small, whereby Comparative Example 4 has an insufficient print density when compared in the same concentration of the coloring matter in an ink (which is 6% by weight as described in the above table 2, for this case) and has a very low vividness, and therefore is still inferior compared with Example 2.

(D-1) Xenon Light Fastness Test of Recorded Image

Using a low temperature xenon weatherometer XL 75 (manufactured by Suga Test Instruments Co., Ltd.), test pieces prepared by printing on glossy papers 1 and 2 were put and irradiated at an illuminance of 100,000 Lux, a humidity of 60% RH and a temperature of 24° C. for 96 hours. The papers were measured for color difference (ΔE) before and after the test in the part thereof where D value was around 1.0, and evaluated. The results are shown in Table 6.

(E) Ozone Gas Fastness Test of Recorded Image

Using an ozone weatherometer (manufactured by Suga Test Instruments Co., Ltd.), test pieces prepared by printing on glossy papers 1 and 2 were left for 8 hours under the circumstances of an ozone concentration of 10 ppm, a humidity of 60% RH and a temperature of 24° C. The papers were measured for color difference (ΔE) before and after the test in the part thereof where D value was around 1.0, and evaluated.

The results are shown in Table 6.

TABLE 6

|  | Light fastness | Ozone gas fastness |
|---|---|---|
| Glossy paper 1 | | |
| Example 2 | 8.5 | 7.4 |
| Comparative Example 1 | 12.2 | 18.4 |
| Comparative Example 2 | 10.3 | 10.6 |
| Comparative Example 3 | 10.5 | 12.5 |
| Comparative Example 4 | 8.0 | 15.3 |
| Glossy paper 2 | | |
| Example 2 | 5.0 | 3.9 |
| Comparative Example 1 | 13.5 | 8.9 |
| Comparative Example 2 | 5.0 | 5.9 |
| Comparative Example 3 | 8.8 | 8.3 |
| Comparative Example 4 | 23.9 | 12.2 |

Judging from Table 6, it is found that Example 2 is excellent in light fastness and ozone gas fastness compared with Comparative Examples 1 to 4, and extremely excellent particularly in ozone gas fastness.

Specifically, with regard to ozone gas fastness, Example 2 has a color difference value of only 3.9 in glossy paper 2; while Comparative Example 4 has a color difference value of 12.2 which is 3 or more times that of Example 2, Comparative Examples 1 and 3 respectively have a color difference value of 8.9 and 8.3 which are twice or more, and Comparative Example 2 having the smallest difference among Comparative Examples has a color difference value of 5.9 which is 1.5 or more times that of Example 2. Similar results are shown in glossy paper 1 although the magnification ratios are different.

In addition, in the light fastness test in glossy paper 1, Example 2 has, a color difference value of 8.5 which stays in 10 or under while any of Comparative Examples 1 to 3 has a value of 10 or more, 10.3 to 12.2; and also in glossy paper 2, Comparative Example 2 has a value of 5.0 which is the same as that of Example 2 while Comparative Example 3 has a value of 8.8 which is 1.7 or more times that of Example 2 and Comparative Example 1 has a value of 13.5 which is 2.7 times that of Example 2. Further, with regard to light fastness in glossy paper 1, Comparative Example 4 has a color difference value of 8.0 which is a slightly more excellent value than 8.5 of Example 2, but in glossy paper 2, it has a color difference value of 23.9 which is 4 or more times that of Example 2 and extremely worse, whereby it cannot be generally used for glossy paper.

(F) Moisture Fastness Test of Recorded Image

Using a thermo-hygrostat (manufactured by Ohken Co., Ltd), test pieces prepared by printing on glossy paper 1 were left at 30° C. and 80% RH for 168 hours. The papers were judged for bleeding property by visual observation before and after the test in the part thereof where D value was around 1.7, resulting that bleeding of any of Example 2 and Comparative Examples 1 to 4 was not observed.

In the moisture fastness test, bleeding of any of Example 2 and Comparative Examples 1 to 4 was not observed in the case of using glossy paper Judging from the above results, the anthrapyridone compound of the present invention is a coloring matter which provides images being properly excellent in all of brightness, hue and vividness and having high fastnesses, and is thus extremely excellent as a magenta coloring matter for inkjet.

The invention claimed is:

1. An anthrapyridone compound represented by the following formula (1) or a salt thereof:

[Formula 1]

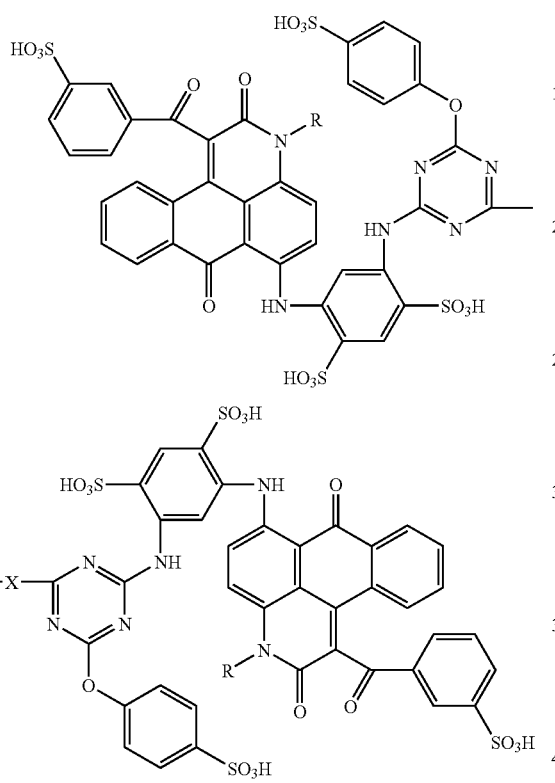

(1)

wherein, R represents a hydrogen atom, an alkyl group, a hydroxy lower alkyl group, a cyclohexyl group or a (mono- or di-alkylamino) alkyl group, and X represents a cross-linking group, respectively.

2. The anthrapyridone compound or a salt thereof according to claim 1, wherein R is a hydrogen atom, a C1 to C4 alkyl group, a hydroxy C1 to C4 alkyl group, a cyclohexyl group or a (mono- or di- C1 to C4 alkylamino) C1 to C4 alkyl group, the cross-linking group X is N,N'-hydrazinediyl or a group selected from the group consisting of the groups represented by the following formulas (201) to (207):

Formula (201)

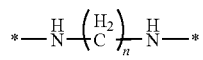

(201)

wherein, n is 2 to 8, and the symbol * represents a binding site to each of two different triazine rings;

Formula (202)

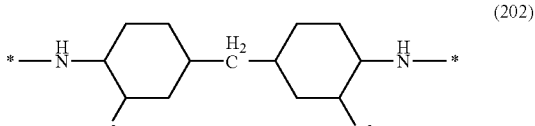

(202)

wherein, $R^2$ represents a hydrogen atom or a methyl group, and the symbol * represents a binding site to each of two different triazine rings;

Formula (203)

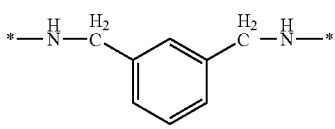

(203)

wherein, the symbol * represents a binding site to each of two different triazine rings;

Formula (204)

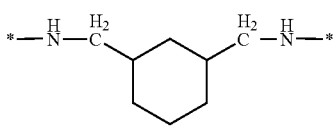

(204)

wherein, the symbol * represents a binding site to each of two different triazine rings;

Formula (205)

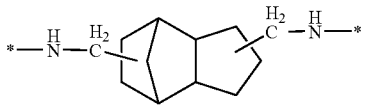

(205)

wherein, the symbol * represents a binding site to each of two different triazine rings;

Formula (206)

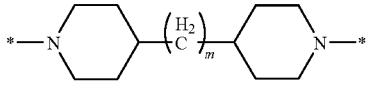

(206)

wherein, m is 2 to 4, and the symbol * represents a binding site to each of two different triazine rings; and Formula (207)

(207)

wherein, the symbol * represents a binding site to each of two different triazine rings.

3. The anthrapyridone compound or a salt thereof according to claim 2, wherein R is a hydrogen atom, a C1 to C4 alkyl group, a hydroxy C1 to C4 alkyl group, a cyclohexyl group or a (mono- or di- C1 to C4 alkylamino) C1 to C4 alkyl group, and X is a group selected from the group consisting of N,N'-hydrazinediyl, the formula (201) where n is 2 to 6, the formula (202), the formula (203), the formula (204), the formula (205), the formula (206) where m is 3, and the formula (207).

4. The anthrapyridone compound or a salt thereof according to claim 3, wherein R is a hydrogen atom, a linear C1 to C4 alkyl group, a 2-hydroxyethyl group, a cyclohexyl group or a 3-diethylaminopropyl group, and X is a group selected from the group consisting of the formula (201) where n is 2 to 4, the formula (202), the formula (203) and the formula (204).

5. The anthrapyridone compound or a salt thereof according to claim 4, wherein R is a hydrogen atom or a linear C1 to C4 alkyl group, and X is a group of the formula (201) where n is 2 to 4.

6. The anthrapyridone compound or a salt thereof according to claim 1, which is represented by the following formula (2):

Formula (2)

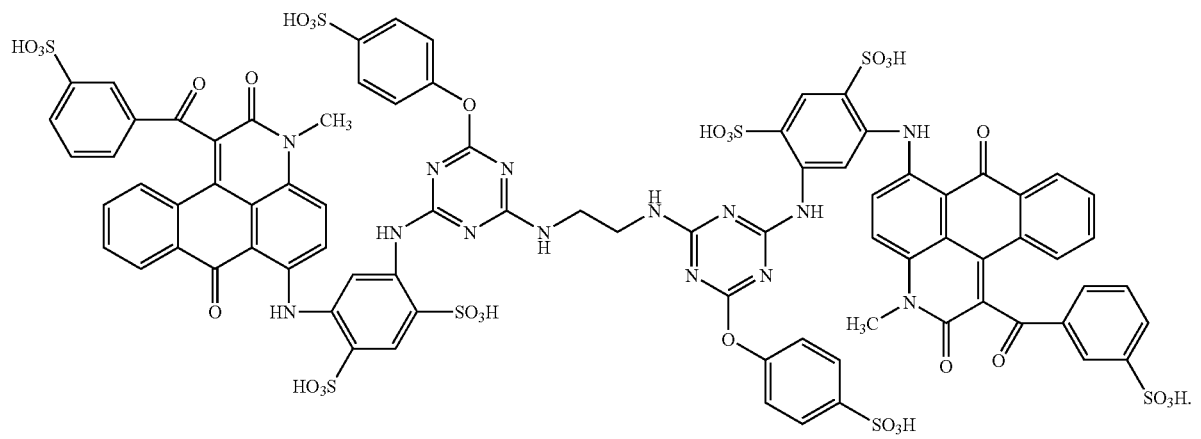
(2)

7. An ink composition comprising the anthrapyridone compound or a salt thereof according to claim 1.

8. The ink composition according to claim 7, which contains water and a water-soluble organic solvent.

9. The ink composition according to claim 8, which is for inkjet recording.

10. The ink composition according to claim 7, wherein the content of an inorganic substance coexisting with the anthrapyridone compound in the total amount of the anthrapyridone compound and the inorganic substance is 1% by weight or less.

11. The ink composition according to claim 7, wherein the content of the anthrapyridone compound is 0.1 to 20% by weight or less.

12. An inkjet recording method comprising discharging droplets of the ink composition according to claim 7 in response to a recording signal to record on a record-receiving material.

13. The inkjet recording method according to claim 12, wherein the record-receiving material is a communication sheet.

14. The inkjet recording method according to claim 13, wherein the communication sheet has an ink receiving layer containing a porous white inorganic substance.

15. A colored product colored with the ink composition according to claim 7.

16. The colored product according to claim 15, wherein coloring is carried out by an inkjet printer.

17. An inkjet printer in which a container containing the ink composition according to claim 7 is installed.

18. The anthrapyridone compound or a salt thereof according to claim 1, wherein in the formula (1), R is a hydrogen atom or a C1 to C4 alkyl group and X is —NH(CH$_2$)$_{2-4}$NH—.

19. An ink composition comprising the anthrapyridone compound or a salt thereof according to claim 18.

20. An ink composition comprising the anthrapyridone compound or a salt thereof according to claim 6.

* * * * *